(12) United States Patent
Nikkola

(10) Patent No.: US 7,129,835 B2
(45) Date of Patent: Oct. 31, 2006

(54) WRIST-TOP COMPUTER

(75) Inventor: Ari Nikkola, Espoo (FI)

(73) Assignee: Suunto Oy, Vantaa (FI)

( * ) Notice: Subject to any disclaimer, the term of this patent is extended or adjusted under 35 U.S.C. 154(b) by 17 days.

(21) Appl. No.: 10/867,649

(22) Filed: Jun. 16, 2004

(65) Prior Publication Data

US 2005/0134451 A1 Jun. 23, 2005

(30) Foreign Application Priority Data

Dec. 19, 2003 (FI) .................................. 20031873

(51) Int. Cl.
*H04B 1/034* (2006.01)
*H04Q 7/00* (2006.01)
*G08B 1/08* (2006.01)

(52) U.S. Cl. ..................... 340/539.11; 340/539.12; 455/100

(58) Field of Classification Search .............. 340/539.1–539.32; 600/503; 702/182–186, 702/160, 176; 482/1–9; 455/575.6, 90.1, 455/100
See application file for complete search history.

(56) References Cited

U.S. PATENT DOCUMENTS

| | | | |
|---|---|---|---|
| 4,703,445 A | 10/1987 | Dassler | |
| 4,736,312 A | 4/1988 | Dassler et al. | |
| 4,962,469 A * | 10/1990 | Ono et al. | ................. 702/160 |
| 5,157,604 A | 10/1992 | Axford et al. | |
| 5,170,161 A | 12/1992 | Sakurai | |
| 5,471,405 A | 11/1995 | Marsh | |
| 5,611,346 A | 3/1997 | Heikkilä et al. | |
| 5,646,593 A * | 7/1997 | Hughes et al. | ........... 340/573.1 |
| 5,891,042 A * | 4/1999 | Sham et al. | ................. 600/483 |
| 5,989,200 A * | 11/1999 | Yoshimura et al. | ......... 600/587 |
| 6,304,774 B1 | 10/2001 | Gorman | |
| 6,332,094 B1 | 12/2001 | Gorman | |
| 6,356,856 B1 * | 3/2002 | Damen et al. | ............... 702/160 |
| 6,898,550 B1 * | 5/2005 | Blackadar et al. | .......... 702/182 |
| 6,989,753 B1 * | 1/2006 | Lamming et al. | ........ 340/573.1 |
| 7,049,954 B1 * | 5/2006 | Terry | ........................ 340/539.1 |
| 2002/0109600 A1 * | 8/2002 | Mault et al. | .............. 340/573.1 |
| 2004/0046658 A1 * | 3/2004 | Turner et al. | ........... 340/539.11 |

FOREIGN PATENT DOCUMENTS

| | | |
|---|---|---|
| DE | 3603-800 A1 | 8/1987 |
| DE | 199 08 993 A1 | 9/2000 |
| WO | WO 92/14999 | 3/1992 |

* cited by examiner

*Primary Examiner*—Daniel Wu
*Assistant Examiner*—Jennifer Mehmood
(74) *Attorney, Agent, or Firm*—Birch Stewart Kolasch & Birch, LLP

(57) ABSTRACT

A method and apparatus in connection with a wristop computer. According to the method, a desired variable is measured using a measuring unit, the measured variable is equipped with at least one digital codeword and transmitted wirelessly over a transfer channel to a receiver, and at the other end of the transfer channel, the transmitter's signal is identified on the basis of at least one codeword. According to the invention, the digital codeword is transmitted to the receiver together with the measured variable depicted as time-period data (t1 or t3).

20 Claims, 3 Drawing Sheets

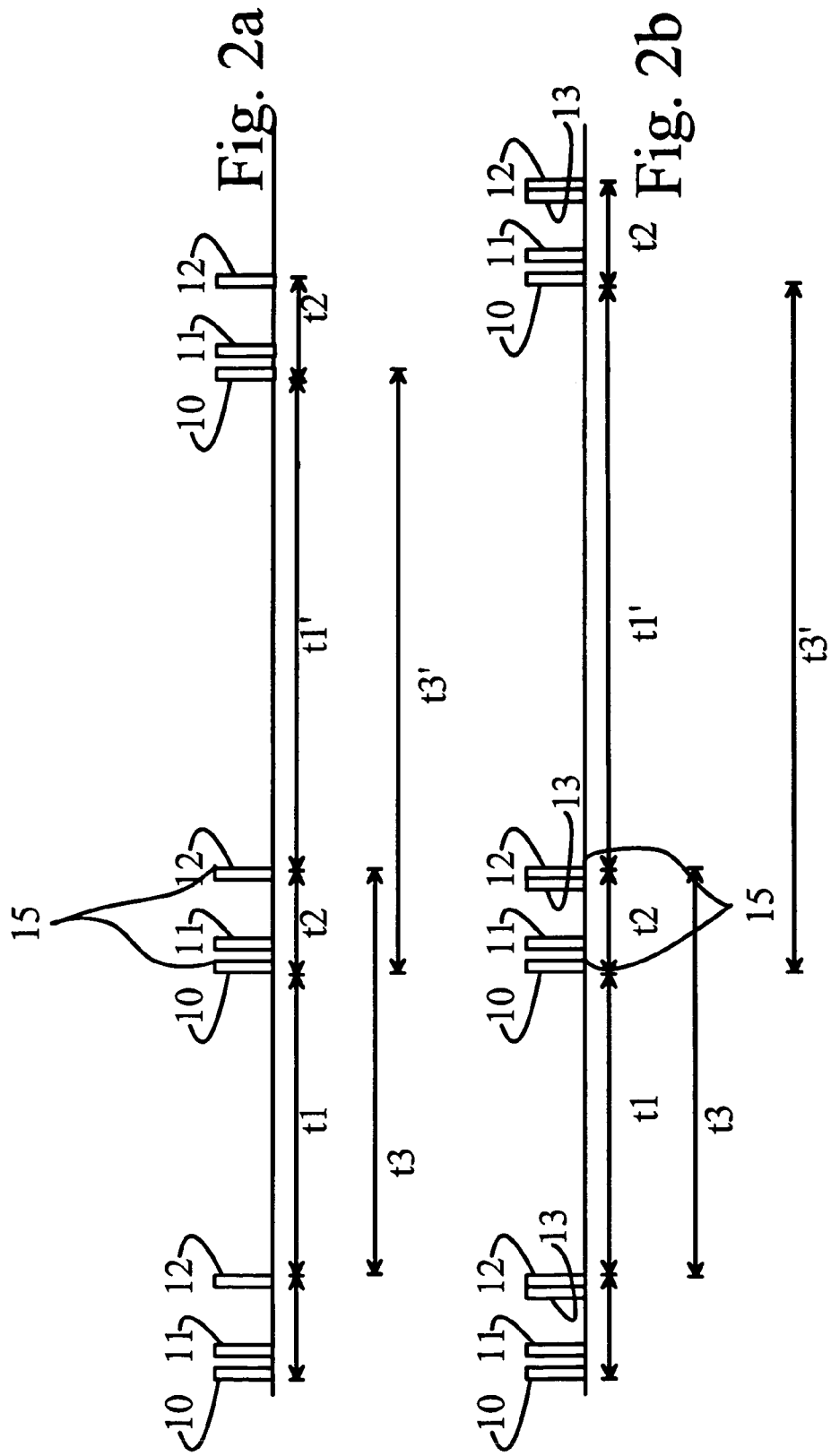

WRIST-TOP COMPUTER

CROSS-REFERENCE TO RELATED APPLICATION

The present application claims priority under 35 U.S.C. §119 to Finnish Patent Application No. 2003-1873, filed Dec. 19, 2003, the entire contents of which are hereby incorporated by reference.

BACKGROUND OF THE INVENTION

1. Field of the Invention

The present invention relates to a data transfer method for wristop computers. The invention also relates to an apparatus for wristop computers.

2. Description of Background Art

According to the state of the art, wristop computers typically include a transmitter belt connected by a flexible belt to a person's body, and which today typically measures pulse. This measuring device equipped with electrodes transmits a measurement message by radio to a wristwatch-like wristop computer, in which at least part of the received signal is processed and shown on the display of the wristop computer.

Wristop computers can be used to measure not only pulse, but also blood pressure, speed, acceleration, distance, and directional data.

If there are several sportspeople close to each other using wristop computers, which typically happens in exercise sessions with instructors, or in mass training events, the receiver must identify the correct transmitter.

According to the prior art, two alternative methods are used to identify the correct transmitter. For instance, Finnish patent 96380 discloses an analog solution, in which the time between at least two identifier pulses is used as the identifier data, by means of which the receiver can select the correct transmission signal from a group of several transmission signals. Implemented using analog technology, this system has been known to lead to error states, if the distance between the identifier pulses of two devices has brought them too close to each other. As a result of interference, for example, it has then been possible for the signals of two transmitters to be mistaken for each other, at least at times.

On the other hand, in newer devices, digital signal transfer with digital identification codes has been used. Though digital data transfer is very reliable, it does, on the other hand, consume a great deal of power in transmitter devices, which are typically battery powered.

SUMMARY AND OBJECTS OF THE INVENTION

The invention is intended to eliminate the defects of the state of the art disclosed above and for this purpose create an entirely new type of solution.

The invention is based on, in data transfer, transmitting the data component of the signal analogically as time data, but using a digital code to code each signal totality being transmitted.

According to one preferred embodiment of the invention, the transmission power required for the code is minimized by using identifier codes that contain as few 1 bits as possible.

According to a second preferred embodiment of the invention, the use is prevented of codes, in which 1-bits, the transmission of which consumes a significant amount of power, form more than 50% of the content.

Considerable advantages are gained with the aid of the invention.

Compared to the analog coding technique, a considerably larger number of transmitter-receiver combinations can be used close to each other, without uncertainty arising as to the receiver for which each signal is intended.

Considerably less transmission power is required compared to purely digital transmission, because, other than the starting and ending pulse, the actual measurement data does not contain energy consuming 1-bits. This gives the transmitter device a considerably longer operating time while using the same battery, than when using other techniques.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 2a shows a timing diagram of one coding method according to the invention.

FIG. 2b shows a second variation of the timing according to the invention.

DETAILED DESCRIPTION OF THE PREFERRED EMBODIMENTS

Figure 1:
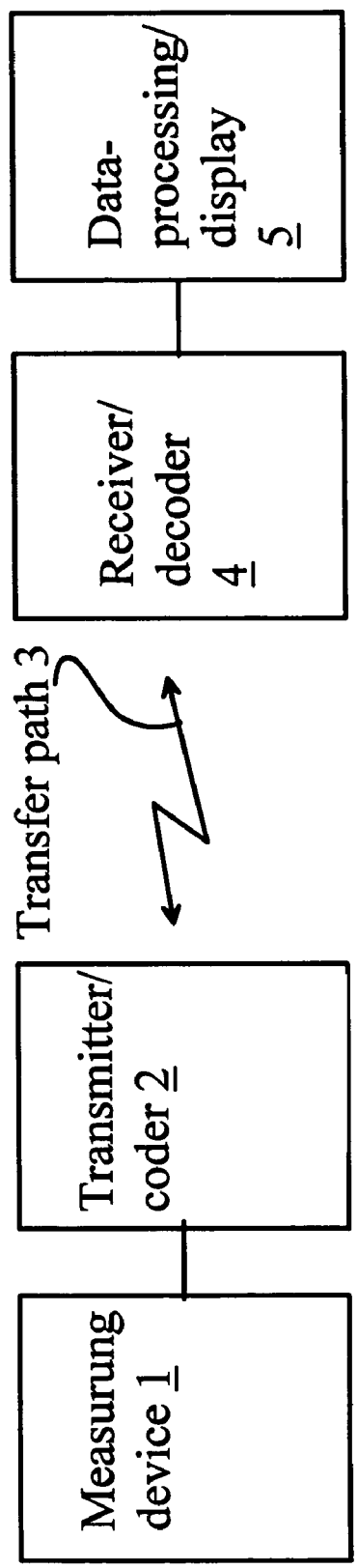
FIG. 1 shows a block diagram of the device environment, to which the invention is applied.

According to FIG. 1, the apparatus includes a measuring device 1, which is typically a pulse meter attached to the chest by a flexible belt. The pulse meter in question contains electrodes, with the aid of which the pulse of the person is measured. The measuring device 1 can naturally be some other measuring device, such as a manometer of a compressed-air bottle in diving equipment, or alternatively a blood-pressure meter. The measuring device is connected to a transmitter/coder 2, in which the measurement signal is edited into a transmittable form and given a code individuating the transmitter 2. The signal is sent from the transmitter 2 wirelessly over a transfer path 3 to a receiver 4, which also includes means for decoding the code. The transfer path 3 is typically the air between the measuring device 2 located around the chest and a receiver located on the wrist, or alternatively the water between a transmitter attached to the compressed-air bottle and the wristop computer.

The receiver 4 is, in turn, connected to a data-processing unit 5, to which a display is typically also connected. The receiver 4 and the data-processing unit 5 are typically implemented in a wristop computer, which is reminiscent of a wristwatch. Such a wristop computer can include not only pulse-measuring properties or other measuring properties, but also normal clock functions, possible positioning equipment, such as GPS circuits, and an altimeter, in which the sensor is typically a pressure sensor, for example, a capacitive pressure sensor.

The wristop computer can also include, for example, a temperature measuring device. Wristop computers are also known, which have connections and data communications devices for connecting a wristop computer to a normal microcomputer, for example, through a USB bus.

According to FIG. 2a, the signal being transmitted includes two repeating time periods, a time period t1 and a time period t2, of which the time period t1 contains the actual measurement information, either directly as the length of the time period, or proportional to the length of this. In the pulse measurement application, t1 is either directly the time between the pulses, or else a time proportional to this. For example, in a pressure measurement application, t1 can also be a period of time proportional to the pressure (the pressure in an oxygen bottle, or blood pressure). The time period t2, in turn, includes a signal identification code, a codeword 15, and a start bit 10, which, according to the invention, is a powered pulse, with a digital value of 1.

This is followed by the desired number of code pulses (bits) as a codeword 15, of which, according to one preferred embodiment of the invention, at most 50% contain energy, in other words, have a value of 1. The other bits have a value of 0. In FIG. 2a, the pulses 11 and 12 represent these energy-containing pulses in an 8-bit codeword 15. The pulse 11 is the second and the pulse 12 the eighth in the code work 15 in question. The number of code bits (=the length of the codeword) can naturally be more or less, however, the number of bits in the codeword 15 typically varies from 4 to 128. Thus, the transmitter's transmission power is on during the pulses 11 and 12 while transmission power is not used during time between these 1-bits.

Thus, in the solution of FIG. 2a, in an eight-bit codeword, the transmission power is on for 25% of the duration of the code. The same principle in terms of power consumption naturally also applies to the time period t1 between the pulses 10 and 12, which represents analog data. Thus, transmission power is not used at all in the time period t1. Thus, t1 can contain, as an analog value, data, for example, on pulses, the periods between pulses, the pressure of an oxygen bottles, pedalling cadence, blood pressure, or speed. At the receiver end, t1 is thus converted into data depicting the variable being measured, by defining the time period t1 as an analog variable, for example with the aid of a gate circuit, during the time between the pulses 10 and 12.

In FIG. 2a, the first time periods t1 and t2 are followed by second time periods t1' and t2, of which t1' in longer than the time period t1.

In turn, FIG. 2b shows, a second alternative solution according to the invention. In this, three bits in a 1 state, which depict the pulses 11, 12, and 13, are used in the time period t2 for coding. In the solution of FIG. 2b, during the codeword 15, transmission power is on for 37.5% of the duration of the codeword.

According to the invention, the time period t1 or t1' can contain data, for instance, on the pressure in a compressed air bottle, or on blood pressure, or on other information used or processed by the wristop computer.

Alternatively, instead of the time periods t1 or t1', the time period data being measured can be the sum t3 of the time periods t1 and t2, or the sum t3' of the time periods t2 and t1', in which case the time t2 used for transmitting the codeword 15 and the start bit is also included in the time period measured.

Figure 3A:
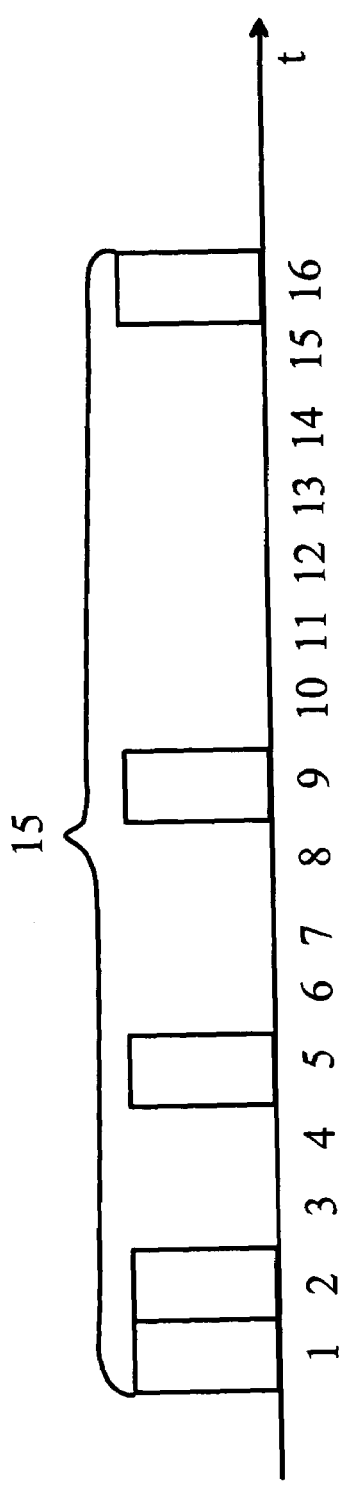
FIGS. 3a–3c show examples of codewords according to the invention.
Figure 3B:
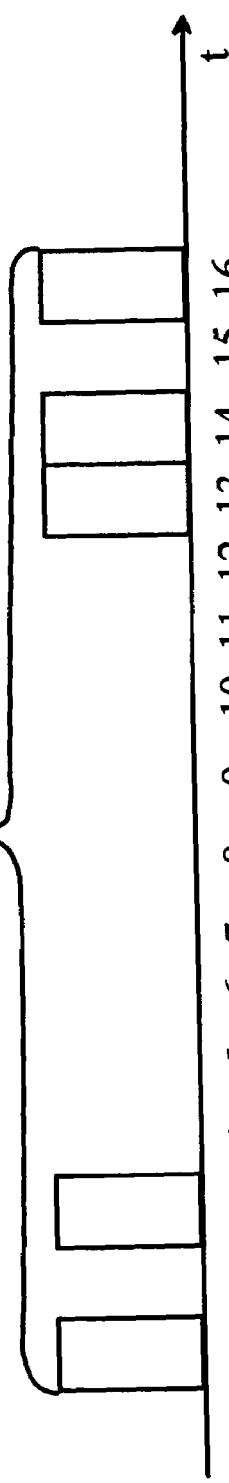
Figure 3C:
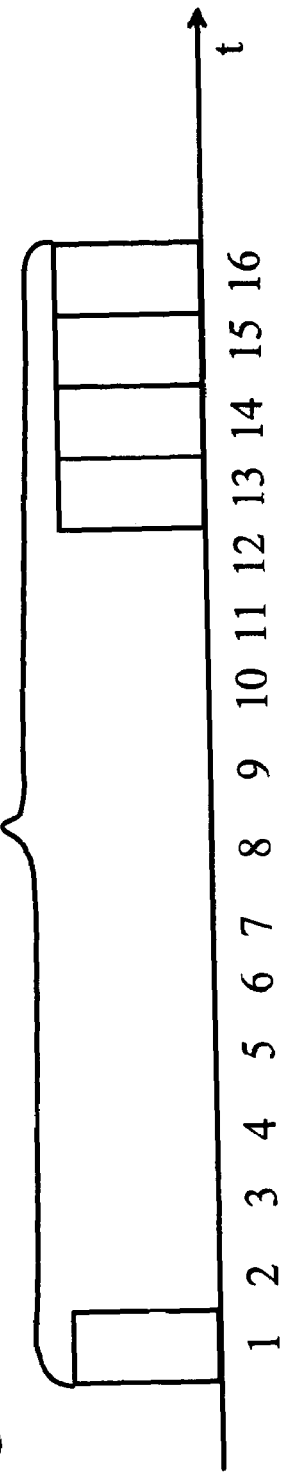

FIGS. 3a–3c show various alternatives of the use of 1-bits in a 16-bit codeword 15. The sequence number of each bit is marked on the time line t. In the example 3a, the bits 2, 3, 5, 9, and 16 have a value of 1.

Correspondingly, in FIG. 3b, the bits 1, 3, 13, 14, and 16 have a value of 1.

Similarly, in FIG. 3c, the 1-bits are the bits 1, 13, 14, 15, and 16.

In some applications (pressure measurement), the measurement period can start with the period t2 containing the identifier code 15.

Thus, according to the invention, the power used for transmission is intended to be minimized by avoiding the transmission of pulses containing power. Thus, even in negative coding (containing 0-bit power) the intention is to similarly avoid bits containing power.

According to the invention, there can even be several consecutive digital codewords 15, one can be, as such, the identifier individuating the transmitting device, the second can be a code stating the type of measurement signal (e.g., acceleration, pulse, etc.), the third can be, for example, error correction, or an error-detection code, which is calculated in a specific manner from the other codes.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A method in connection with a wrist-top computer, in which
   measuring a desired variable using a measuring unit,
   equipping the measured variable with at least one digital code word;
   transmitting the measured variable with the at least one digital code word wirelessly over a transfer channel to a receiver, and
   at the other end of the transfer channel, identifying the transmitted signal based on a digital code word,
   wherein
   the digital code word is transmitted to the receiver together with the measured variable depicted as time-period data (t1 or t3)
   wherein fewer than 50% of a total number of bits of the code word are permitted as power-containing bits in the digital code word.

2. A method according to claim 1, wherein there are as few bits containing power as possible are used in the digital code word.

3. A method according to claim 1, wherein a maximum of 37.5% of a total number of bits of the code word are permitted as power-containing bits in the digital code word.

4. A method according to claim 1, wherein at most two bits containing power are used in the code word.

5. A method according to claim 1, wherein the code word has eight bits.

6. A method according to claim 1, wherein, after measuring the desired variable, transmitting several consecutive code words to the receiver, the several consecutive code words including two or more of a device ID code, a code identifying a type of measurement, and an error-correction code.

7. A method according to claim 1, further comprising the step of transmitting the code word after a measurement period (t1).

8. An apparatus in connection with a wrist-top computer, which apparatus includes
   a measuring unit for measuring a desired variable,
   a transmitter/coder connected to the measuring unit, for equipping the measured variable with a digital code word and transmitting it to a transfer channel,
   a receiver for receiving a signal from the transfer channel,
   a data-processing unit for processing the received signal, wherein
   the transmitter and receiver apparatuses include means for processing the code word in a digital form and for processing the measurement variable as time-period data (t1 or t3),
   wherein fewer than 50% of a total number of bits of the code word are permitted as power-containing bits in the digital code word.

9. An apparatus according to claim 8, wherein the apparatus includes means for minimizing the bits containing power in the digital code word.

10. An apparatus according to claim 8 or 9, wherein the apparatus includes means for permitting only 37.5% of a total number of code bits are bits containing power in the digital code word.

11. An apparatus according to claim 8, wherein, at most, two bits containing power in the code word are used in the apparatus.

12. An apparatus according to claim 8, wherein the code word has eight bits.

13. An apparatus according to claim 8, wherein, after the measuring the desired variable, the apparatus is adapted to transmit several consecutive code words to the receiver, the several consecutive code words including two or more of a device ID code, a code identifying a type of measurement, and an error-correction code.

14. A method according to claim 1, further comprising the step of transmitting the code word from one measurement period concurrently with a next measurement period.

15. A method according to claim 1, wherein the desired variable is pressure of an oxygen bottle.

16. A method according to claim 1, wherein one of the power-containing bits is a last bit in the code word.

17. An apparatus according to claim 8, wherein the code word from one measurement period is transmitted concurrently with a next measurement period.

18. An apparatus according to claim 8, wherein the desired variable is pressure of an oxygen bottle.

19. An apparatus according to claim 8, wherein one of the power-containing bits is a last bit in the code word.

20. An apparatus according to claim 1, further comprising the step of immediately transmitting additional measured variables the at least one digital code word upon completion of the step of transmitting an initial measured variable with the at least one digital code word.

* * * * *